(12) United States Patent
Kalender et al.

(10) Patent No.: US 8,199,993 B2
(45) Date of Patent: Jun. 12, 2012

(54) METHOD FOR DEFINING AN INDIVIDUAL COORDINATION SYSTEM FOR A BREAST OF A FEMALE PATIENT

(75) Inventors: Willi Kalender, Moehrendorf (DE); Harry Schilling, Eichstaett (DE)

(73) Assignee: MIR Medical Imaging Research Holding GmbH, Moehrendorf (DE)

( * ) Notice: Subject to any disclaimer, the term of this patent is extended or adjusted under 35 U.S.C. 154(b) by 574 days.

(21) Appl. No.: 12/401,976

(22) Filed: Mar. 11, 2009

(65) Prior Publication Data
US 2010/0080347 A1    Apr. 1, 2010

(30) Foreign Application Priority Data
Sep. 29, 2008  (DE) .......................... 10 2008 042 430

(51) Int. Cl.
   *G06K 9/34*       (2006.01)
(52) U.S. Cl. ........................... 382/131; 382/132; 378/37
(58) Field of Classification Search .................. 382/128, 382/130, 131, 132; 378/37
   See application file for complete search history.

(56) References Cited

U.S. PATENT DOCUMENTS

| | | |
|---|---|---|
| 3,673,394 A | 6/1972 | Hartmann |
| 4,015,836 A | 4/1977 | Redington et al. |
| 4,400,827 A | 8/1983 | Spears |
| 4,680,028 A | 7/1987 | Stuart |
| 4,709,382 A | 11/1987 | Sones |
| 5,273,435 A | 12/1993 | Jacobson |
| 5,308,321 A | 5/1994 | Castro |
| 5,386,447 A | 1/1995 | Siczek |
| 5,426,685 A | 6/1995 | Pellegrino et al. |
| 5,528,043 A | 6/1996 | Spivey et al. |
| 5,569,266 A | 10/1996 | Siczek |
| 5,609,827 A | 3/1997 | Russell et al. |
| 5,664,569 A | 9/1997 | Damadian et al. |
| 5,709,206 A * | 1/1998 | Teboul .......................... 600/437 |
| 5,757,878 A | 5/1998 | Dobbs et al. |
| 5,803,912 A | 9/1998 | Siczek et al. |

(Continued)

FOREIGN PATENT DOCUMENTS

DE    19639975    5/1998

(Continued)

OTHER PUBLICATIONS

Zikuan Chen and Ruola Ning, "Why should breast tumour detection go three dimensional?," Phys. Med. Biol. 48, (2003), 2217-2228.*

(Continued)

*Primary Examiner* — Allen C. Ho
(74) *Attorney, Agent, or Firm* — Kevin L. Daffer; Daffer McDaniel, LLP

(57) ABSTRACT

A method is provided for determining a position of an object within a breast of a female patient in a simple manner from a three-dimensional image taken of the breast. A simplified model is made of an internal structure of a breast having glandular bodies leading via lactiferous ducts to an outlet at a nipple. A particularly advantageous model is a tree-type structure in which branches correspond to lactiferous ducts and leaves correspond to glandular bodies. Furthermore, a determination is made of whether the object has contact with an element of the tree-type structure. Alternatively, a distance to an element of the tree-type structure is established. By correlating tree-type structures derived from various images taken on the same breast, the location of the object can be unequivocally established.

19 Claims, 3 Drawing Sheets

U.S. PATENT DOCUMENTS

| | | | |
|---|---|---|---|
| 6,242,743 B1 | 6/2001 | DeVito et al. | |
| 6,254,614 B1 | 7/2001 | Jesseph | |
| 6,298,114 B1 | 10/2001 | Yoda | |
| 6,325,537 B1 | 12/2001 | Watanabe | |
| 6,358,246 B1 | 3/2002 | Behl et al. | |
| 6,415,012 B1 | 7/2002 | Taguchi et al. | |
| 6,418,188 B1 | 7/2002 | Broadnax | |
| 6,419,390 B1 | 7/2002 | Landis-Lowell | |
| 6,463,122 B1 | 10/2002 | Moore | |
| 6,480,565 B1 | 11/2002 | Ning | |
| 6,614,921 B1 * | 9/2003 | Chung et al. | 382/131 |
| 6,684,097 B1 | 1/2004 | Parel et al. | |
| 6,819,736 B1 | 11/2004 | Bruder et al. | |
| 6,837,772 B1 | 1/2005 | Luk | |
| 6,872,001 B1 | 3/2005 | Gilevich | |
| 7,005,988 B2 | 2/2006 | Mathewson, II et al. | |
| 7,065,393 B2 | 6/2006 | Sati et al. | |
| 7,149,566 B2 * | 12/2006 | Lee | 600/429 |
| 7,218,766 B2 * | 5/2007 | Eberhard et al. | 382/132 |
| 7,229,440 B2 * | 6/2007 | Ho et al. | 606/47 |
| 7,304,578 B1 | 12/2007 | Sayers et al. | |
| 7,453,978 B1 | 11/2008 | DiBianca et al. | |
| 7,467,892 B2 | 12/2008 | Lang et al. | |
| 7,492,858 B2 | 2/2009 | Partain et al. | |
| 7,519,209 B2 * | 4/2009 | Dawant et al. | 382/128 |
| 7,556,426 B2 | 7/2009 | Nakajo et al. | |
| 7,558,370 B2 | 7/2009 | Sommer, Jr. et al. | |
| 7,643,670 B2 * | 1/2010 | Leach et al. | 382/154 |
| 7,653,229 B2 * | 1/2010 | Kaufhold et al. | 382/131 |
| 7,677,799 B2 | 3/2010 | Jensen et al. | |
| 7,697,660 B2 | 4/2010 | Ning | |
| 7,743,953 B2 | 6/2010 | Okazaki et al. | |
| 7,764,765 B2 | 7/2010 | Ohta et al. | |
| 7,778,388 B2 * | 8/2010 | Sendai | 378/22 |
| 7,783,089 B2 * | 8/2010 | Kaufhold et al. | 382/128 |
| 7,783,094 B2 * | 8/2010 | Collins et al. | 382/128 |
| 7,840,046 B2 * | 11/2010 | Jerebko et al. | 382/128 |
| 7,850,613 B2 | 12/2010 | Stribling | |
| 7,940,966 B2 * | 5/2011 | Yu et al. | 382/128 |
| 8,014,576 B2 * | 9/2011 | Collins et al. | 382/128 |
| 2002/0181651 A1 | 12/2002 | Shepherd et al. | |
| 2003/0072409 A1 | 4/2003 | Kaufhold et al. | |
| 2003/0204965 A1 | 11/2003 | Hennessey | |
| 2004/0066880 A1 | 4/2004 | Oikawa | |
| 2004/0082856 A1 | 4/2004 | Marmarelis | |
| 2004/0092826 A1 | 5/2004 | Corbeil et al. | |
| 2004/0238750 A1 | 12/2004 | Vafi et al. | |
| 2004/0251419 A1 | 12/2004 | Nelson et al. | |
| 2004/0254461 A1 | 12/2004 | Ackerman, III | |
| 2005/0070817 A1 | 3/2005 | Mueller, Jr. | |
| 2006/0094950 A1 | 5/2006 | Ning | |
| 2006/0145871 A1 | 7/2006 | Donati et al. | |
| 2006/0262898 A1 | 11/2006 | Partain et al. | |
| 2007/0009080 A1 | 1/2007 | Mistretta | |
| 2007/0064867 A1 | 3/2007 | Hansen et al. | |
| 2007/0092059 A1 | 4/2007 | Eberhard et al. | |
| 2007/0237306 A1 | 10/2007 | Jones et al. | |
| 2007/0238957 A1 | 10/2007 | Yared | |
| 2008/0033420 A1 | 2/2008 | Nields et al. | |
| 2008/0037703 A1 | 2/2008 | Ting | |
| 2008/0081984 A1 | 4/2008 | Lafferty | |
| 2008/0084961 A1 | 4/2008 | Keppel et al. | |
| 2008/0089471 A1 | 4/2008 | Kobayashi | |
| 2008/0101538 A1 | 5/2008 | Schliermann | |
| 2008/0187095 A1 | 8/2008 | Boone et al. | |
| 2008/0205588 A1 | 8/2008 | Kim | |
| 2008/0221443 A1 | 9/2008 | Ritchie et al. | |
| 2008/0221478 A1 | 9/2008 | Ritchie et al. | |
| 2008/0230074 A1 | 9/2008 | Zheng et al. | |
| 2009/0080604 A1 | 3/2009 | Shores et al. | |
| 2009/0196393 A1 | 8/2009 | Wang et al. | |
| 2010/0080343 A1 | 4/2010 | Kalender et al. | |
| 2010/0080344 A1 | 4/2010 | Schilling et al. | |
| 2010/0080345 A1 | 4/2010 | Schilling et al. | |
| 2010/0080346 A1 | 4/2010 | Kalender et al. | |
| 2010/0080348 A1 | 4/2010 | Kalender et al. | |
| 2010/0080349 A1 | 4/2010 | Kalender et al. | |
| 2010/0080350 A1 | 4/2010 | Kalender et al. | |
| 2010/0128843 A1 | 5/2010 | Tita | |

FOREIGN PATENT DOCUMENTS

| | | |
|---|---|---|
| DE | 19812995 | 10/1999 |
| DE | 10026792 | 12/2001 |
| DE | 10207623 | 11/2003 |
| DE | 102004042790 | 3/2006 |
| DE | 102005022347 | 11/2006 |
| DE | 102005048049 | 4/2007 |
| EP | 0435837 | 7/1991 |
| EP | 1549115 | 6/2005 |
| EP | 1700568 | 9/2006 |
| EP | 1864611 | 12/2007 |
| JP | 2008272093 | 11/2008 |
| WO | 93/17620 | 9/1993 |
| WO | 94/06352 | 3/1994 |
| WO | 98/49939 | 11/1998 |
| WO | 99/30615 | 6/1999 |
| WO | 2004/006755 | 1/2004 |
| WO | 2004/043535 | 5/2004 |
| WO | 2006/119426 | 11/2006 |
| WO | 2007/120622 | 10/2007 |
| WO | 2008/024611 | 2/2008 |
| WO | 2008/054279 | 5/2008 |

OTHER PUBLICATIONS

Michael Kass et al., "Snakes: Active Contour Models," International Journal of Computer Vision, 321-331 (1988).*
Notice of Allowance mailed Dec. 14, 2010 for U.S. Appl. No. 12/401,735.
Minhaj et al., "Laser interstitial thermotherapy (LITT) monitoring using high-resolution digital mammography: theory and experimental studies," Physics in Medicine and Biology, vol. 47, 2002, pp. 2987-2999.
Notice of Allowance mailed Mar. 8, 2011 for U.S. Appl. No. 12/402,225.
Final Office Action mailed Feb. 23, 2011 for U.S. Appl. No. 12/401,792.
Mun et al., "Active RFID System Augmented with 2D Barcode for Asset Management in a Hospital Setting," IEEE International Conference on RFID, Mar. 2007, pp. 205-211.
Nishide et al., "Micro-focus x-ray CT imaging of breast specimens with microcalcifications," 89th Scientific Assembly and Annual Meeting of the Radiological Society of North America, Dec. 2003, pp. 1662-1663.
Tornai et al., "Design and Development of a Fully-3D Dedicated X-ray Computed Mammotomography System," Proceedings of SPIE, vol. 5745, 2005, pp. 189-197.
Bentzen et al., "Isotherm mapping in hyperthermia using subtraction X-ray computed tomography," Radiotherapy and Oncology, vol. 2, 1984, pp. 255-260.
Griffiths et al., "Applied potential tomography for non-invasive temperature mapping in hyperthermia," Clin. Phys. Physiol. Meas., Vol. 8, Suppl. A, 1987, pp. 147-153.
Jenne et al, "CT On-Line Monitoring of HIFU Therapy," IEEE Ultrasonics Symposium, 1997, pp. 1377-1380.
Fallone et al., "Noninvasive thermometry with a clinical x-ray CT scanner," Med. Phys., vol. 9, No. 5, 1982, pp. 715-721.
Office Action mailed Nov. 3, 2009 for U.S. Appl. No. 12/401,765.
Notice of Allowance mailed Apr. 15, 2010 for U.S. Appl. No. 12/401,765.
Office Action mailed Apr. 14, 2010 for U.S. Appl. No. 12/402,059.
Office Action mailed Apr. 1, 2010 for U.S. Appl. No. 12/402,141.
Office Action mailed May 3, 2011 for U.S. Appl. No. 12/401,792.
Office Action mailed Jun. 10, 2010 for U.S. Appl. No. 12/401,735.
Office Action mailed Jun. 16, 2010 for U.S. Appl. No. 12/401,906.
Office Action mailed Jul. 13, 2010 for U.S. Appl. No. 12/402,225.
Office Action mailed May 11, 2010 for U.S. Appl. No. 12/401,814.
Notice of Allowance mailed Aug. 23, 2010 for U.S. Appl. No. 12/401,765.
Notice of Allowance mailed Sep. 17, 2010 for U.S. Appl. No. 12/402,059.
Office Action mailed Sep. 23, 2010 for U.S. Appl. No. 12/401,792.
Notice of Allowance mailed Sep. 29, 2010 for U.S. Appl. No. 12/401,814.

* cited by examiner

METHOD FOR DEFINING AN INDIVIDUAL COORDINATION SYSTEM FOR A BREAST OF A FEMALE PATIENT

PRIORITY CLAIM

This application claims priority to pending German Application No. DE 102008042430.7 filed on Sep. 29, 2008.

BACKGROUND OF THE INVENTION

1. Field of the Invention

The invention relates to a diagnostic method for application to a female breast. It makes possible a determination of a position of an object within the breast by evaluation of three-dimensional images of the breast, as produced for example by a CT scanner.

2. Description of Related Art

Various instruments such as X-ray machines or also computed tomography (CT) scanners are known for examining a female breast. A CT scanner of this kind is described, for example, in U.S. Patent Application Publication No. 2006/0094950, now U.S. Pat. No. 7,697,660. An X-ray facility with a rotating gantry which has an X-ray tube and a detector is located below a patient table on which a patient to be examined rests. A breast of the patient to be examined projects through an opening in the patient table and into a ray path of the X-ray facility. In order to create constant conditions during an examination, the breast to be examined is pushed upwards with a pushing implement and put into a predefined cylinder-like shape. An adaptation to various breast sizes is possible by shifting the implement. Another device for stabilizing a breast of a patient is disclosed in U.S. Pat. No. 6,418,188. A cup of rubber-like fabric is positioned to cover a breast, and is then drawn away from the patient by means of a cord. The diameter of the breast is thereby compressed and the breast is elongated. By means of vacuum fixation systems as disclosed in European Patent Application Publication No. 1864611, a breast is drawn into a bowl-shaped vessel by sub-pressure.

With the disclosed different devices for locating in the sense of fixing or positioning a breast, the breast is in each case put into a different shape. Furthermore, the shape of the breast in the fixing means can differ from one application to the next. It is almost impossible to determine the location of a particular object within the breast because the object is urged into a different position according to the device and the shaping in each particular case.

BRIEF SUMMARY OF THE INVENTION

The following description of the objective of the disclosure provided herein and the descriptions of embodiments of a method and a system for determining a position of an object within a breast of a female patient is not to be construed in any way as limiting the subject matter of the appended claims.

The objective of the method described herein is to provide a method which is reproducible for determining a position of an object, for example a tumor, within a breast of a female patient and which is independent of an instrument used to image the breast. It is another object to design an X-ray CT scanner so that the position of an object within a breast of a female patient can be determined.

An embodiment of a method for determining a position of an object within a breast of a female patient includes producing a three-dimensional image of the breast, identifying lactiferous ducts and associated glandular bodies in the image, and determining the position of the object relative to at least one of the lactiferous ducts and glandular bodies. An embodiment of an X-ray machine includes program instructions which are executable by a processor for such process steps.

BRIEF DESCRIPTION OF THE DRAWINGS

In the following, the invention will be described by way of example, without limitation of the general inventive concept, on examples of embodiments and with reference to the drawings.

Figure 1:
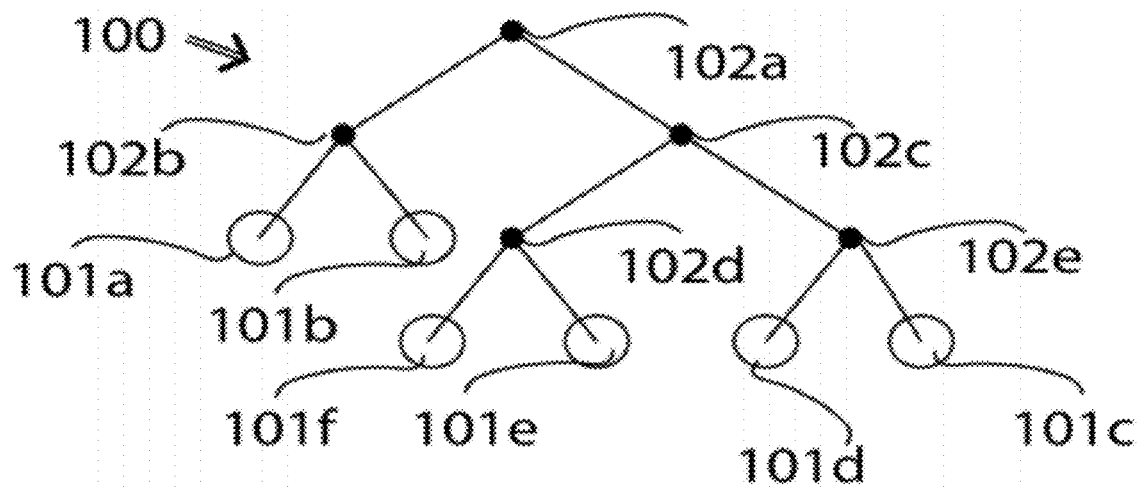
FIG. 1 shows an example of a tree-type structure generated from an imaged inner structure of a female breast.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

Figure 2:
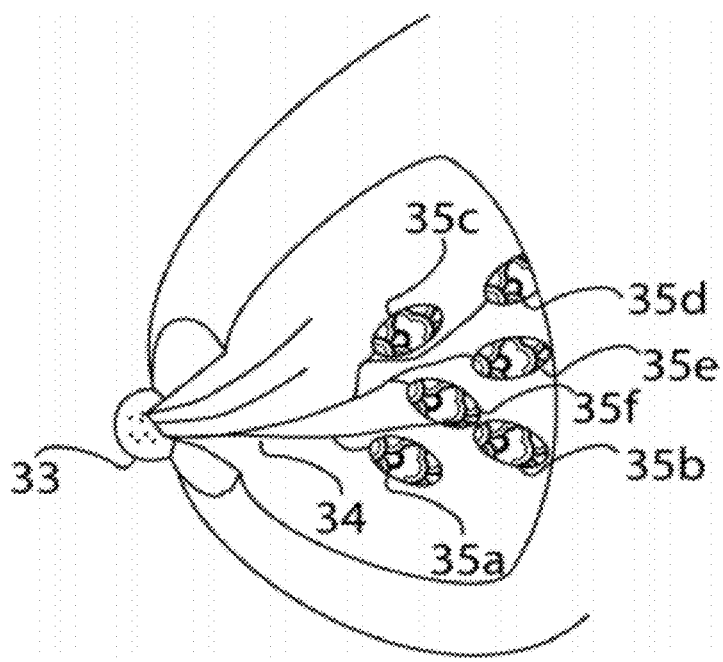
FIG. 2 schematically shows an example of an inner structure of a female breast.

FIG. 1 shows a tree-type structure 100 as can be produced with the method described herein. FIG. 2 schematically shows an inner structure of a female breast from which this tree-type structure has been produced. The uppermost node 102a of the tree-type structure corresponds to the position of the breast nipple 33. Starting out from this node, there follows in the left branch another node 102b with leaves 101a and 101b. These leaves correspond to glandular bodies 35a and 35b on a mammary or lactiferous duct 34. Starting again from the uppermost node, in the right branch the node 102c is followed on the left by the node 102d with the leaves 101f corresponding to the glandular body 35f and 101e corresponding to the glandular body 35e, and on the right by the node 102e with the leaves 101d corresponding to the glandular body 35d, and 101c corresponding to the glandular body 35c. For an exact localization, additional features such as the size of the mammary glands, e.g. the volume or the idealized half-axes of an ellipsoid are stored in a memory. Similarly, the distance from node to node or from node to leaf in the tree can be also stored.

Figure 3:
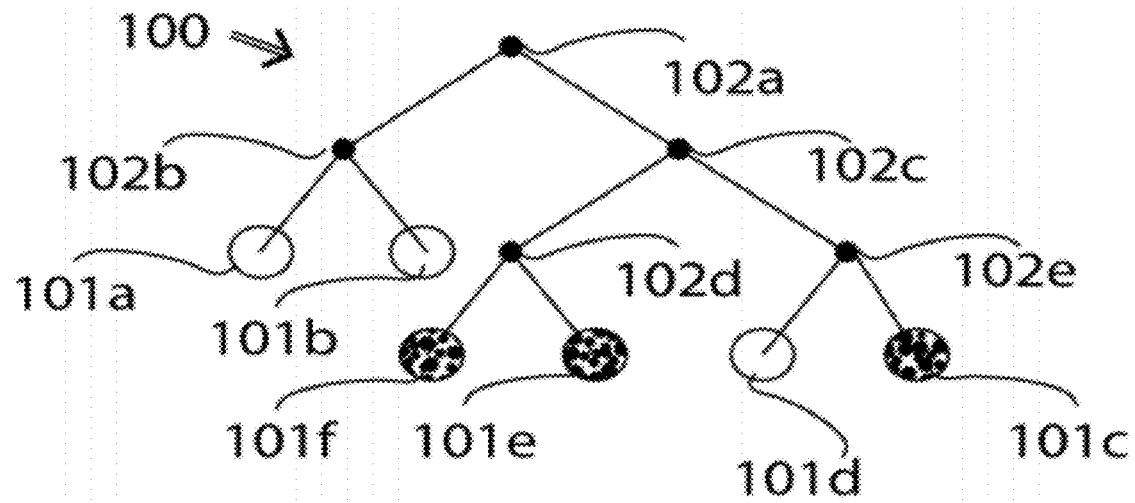
FIG. 3 shows an example of a tree-type structure generated from an imaged inner structure of a breast with a tumor.

For identification of a tumor, the number of calcified micro deposits in the tumor can be stored. These may be determined by simple threshold segmentation and cluster formation. FIG. 3 shows a tree-type structure corresponding to the schematically illustrated breast of FIG. 4 with a tumor 37. This tumor touches the glandular bodies 35c, 35e, and 35f. The leaves 101c, 101e, and 101f are marked accordingly. In a simplest case, only one single bit is set, which signals contact with a tumor. Alternatively, however, a number or another identification mark for a certain tumor could be stored here. If now a new three-dimensional image is made of the breast at a later date, and a tree-type structure is determined from this, then it may be concluded that now the tumor again touches the leaves 101*c*, 101*e*, and 101*f* corresponding to the glandular bodies 35*c*, 35*e*, and 35*f*. As the position of these glandular bodies is already known from the tree-type structure, the position of the tumor also may be determined in a simple manner.

Figure 4:
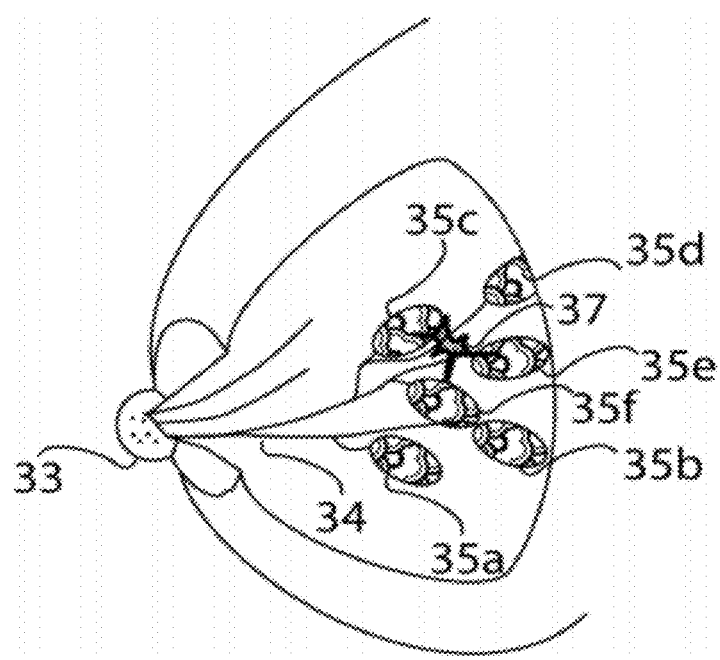
FIG. 4 schematically shows an example of an inner structure of a breast with a tumor.
Figure 5:
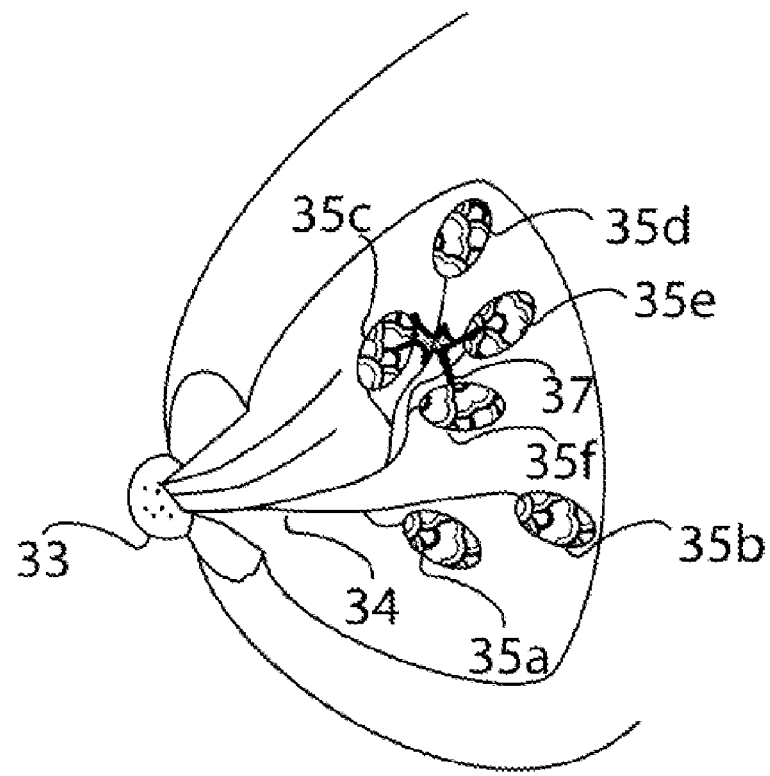
FIG. 5 schematically shows an example of the inner structure of the breast of FIG. 4 in a different image.

FIG. 5 schematically shows the inner structure of the breast of FIG. 4 from another image. Although the same breast is concerned in the previous figure, here some of the glandular bodies are at a different location. In particular, the glandular bodies 35*c*, 35*d*, 35*e*, 35*f*, and also the tumor 37 are displaced upwardly. As can be well discerned, the basic structure is not changed. The associated tree corresponds to the tree 100 of FIG. 3 and is identical with the tree concerning the illustration of FIG. 4. Here too, an exact localization of the tumor is possible, because it touches the glandular bodies 35*c*, 35*e* and 35*f* in the same way as in FIG. 4. A displacement of glandular bodies or also of a tumor can be effected by different positioning of the breast or also by time-staggered images. A different arrangement in the images will arise particularly with different X-ray machines. The tree-type structure based on the glandular bodies and the lactiferous ducts is always constant and, therefore, makes possible a comparison of various images.

Figure 6:
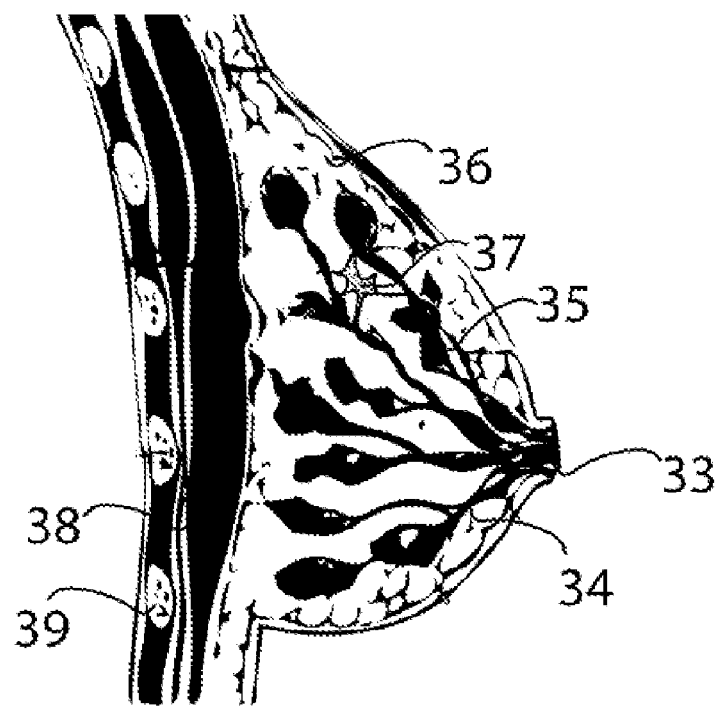
FIG. 6 shows an example of an inner structure of a breast.

FIG. 6 shows also a schematic structure of a female breast. The individual glandular bodies (*Lobuli glandulae mammariae*) 35 are connected with the nipple (*Papilla mammaria*) 33 via lactiferous ducts (*ductus lactiferus*) 34. Interglandular fatty tissue 36 or connective tissue is located between individual glandular bodies. A tumor is marked by reference number 37. The breast lies on the breast muscle (*Musculos pectoralis* major) 38 which in turn rests on the ribs 39.

A method described herein for determining the position of an object (e.g., tumor 37) within a breast of a female patient is based on a spatial assignment of the object to the inner structure of the breast. A human female breast has 15 to 20 lactiferous ducts in the nipple, extending into the breast to a multitude of glandular bodies. The combination of the lactiferous ducts and glandular bodies results in a complex structure which is unique for each breast. This structure remains basically unchanged, even when the shape of the breast is changed from the outside, for example by a fixing device. Thus, with the aid of a three-dimensional image of the breast, an object (e.g., a tumor) can be assigned within the structure. If it is desired to rediscover this object later in another three-dimensional image which has been made at a later time and/or with another instrument with another fixing device for the breast, then the inner structure of the breast is analyzed with the aid of the three-dimensional image. Now it is possible to determine in simple manner the position of the object by correlation with the breast structure of the previous image.

A corresponding method includes preparing a three-dimensional image of the breast. This three-dimensional image of the breast may be prepared, for example, by means of an X-ray CT machine, and/or with an ultrasonic scanner, and/or with a nuclear spin tomograph. It is of particular advantage for this image to be made at high soft-part contrast and at high local resolution. The method further includes identifying the lactiferous ducts and also the associated glandular bodies within the three-dimensional image. For an identification of the lactiferous ducts, it is advantageous to first perform a threshold value segmentation of the lactiferous ducts. Thus, a gray scale range may be selected from the three-dimensional image, in which lactiferous ducts are shown. For an exact identification of the course of lactiferous ducts, a geometrical segmentation is subsequently performed. An identification of the lactiferous ducts is effected, for example, with a Snakes algorithm or another contour-finding algorithm. Furthermore, for this, knowledge of geometrical shapes of lactiferous ducts and glandular bodies may be used. In addition, the method includes determining a position of an object within a breast with reference to the lactiferous ducts or glandular bodies of the breast. For determining the position of an object within a breast, the spatial relationship between the object and the internal structure of the breast, i.e. the lactiferous ducts and the glandular bodies, can now be used. Preferably, it is determined with which glandular bodies and/or lactiferous ducts the object is in contact. As an alternative to this, the distance of the object from neighboring glandular bodies and/or lactiferous ducts also can be determined and evaluated. For this, it is of special advantage for the internal structure of the breast to be transposed to or converted into a simplified model. This model can be represented, for example, as a graphic vector representation or as a tree-type structure.

In an additional step, it is also possible to identify the nipple in the image. With this, the reliability and reproducibility of the method can be further enhanced. This step is preferably performed in connection with the process of identifying the lactiferous ducts and the associated glandular bodies within the image, i.e., directly preceding, during, or directly following such a process. As the nipple is a basic structural element of a breast, it can be identified with relatively small effort in a three-dimensional image. For this, a contour segmentation of the breast is preferably effected. With this, the boundary of a breast is determined against a background. Here, however, the nipple can also be identified with additional geometrical considerations based on the basic shape of a breast, such as the fact that the nipple faces away from the breast wall of the patient. Should it not be identifiable by its contour in the three-dimensional image, then it may be indirectly discernable from internal structural features such as, for example, the end of a multitude of lactiferous ducts.

The tree-type structure (i.e., a tree-shaped data structure as can be produced with a computer program) is a particularly elegant model. Here, the branches of the tree-type structure correspond to the lactiferous ducts, and the leaves correspond to the glandular bodies. Now in order to define the position of the object, the geometrical or spatial assignment of the object to lactiferous ducts and/or glandular bodies is determined. A particularly simple way of performing a spatial assignment is that of direct contact. As the individual glandular bodies are densely packed inside a breast, an object inside a breast will always have direct contact with at least one glandular body. Another way of performing a spatial assignment makes use of the distance from a glandular body or also from a branch in a lactiferous duct. Preferably, the distance from the center of mass of a glandular body is used here. This center of mass can be determined with relative accuracy on the basis of an integration with respect to the volume of the glandular body. Its determination is at least more exact than a detailed determination of the outer contour of the glandular body.

For comparison of a three-dimensional image of a breast with another three-dimensional image of the same breast, it is necessary for the generated models and, in particular, the tree-type structures to be rendered consistent with each other. In many cases, it will be already sufficient to compare the basic tree-type structure, i.e. the structure of the individual branches with each other. In order to exclude ambiguities, however, additional features may be compared. Such features may be, for example, the lengths of individual lactiferous ducts in total or between branches, the sizes of glandular bodies, or also the distances of lactiferous ducts and/or glandular bodies from other lactiferous ducts and/or glandular bodies, and the vicinity of other lactiferous ducts and glandular bodies. Another feature could be, for example, the arrangement of the lactiferous ducts at the nipple. In some embodiments, a plurality of such features are combined with each other. If the two models derived from two three-dimensional images are rendered consistent, then positional information on the object relative to the breast structure obtained from the first model can be transposed to the second model derived from the three-dimensional image. Thus, the position of the object in the second model may be determined.

Another way of achieving comparability of different three-dimensional images is to set up standardized models or tree-type structures. Thus, a tree-type structure could be built-up starting from a particular glandular body located close to a breast wall, which can hardly be moved even by a displacement of the breast. The arrangement of the remaining tree-type structure would result from the positions relative to this particular glandular body. Alternatively, the tree-type structure could also be built-up starting with the shortest or longest lactiferous duct. Another way would be a sorting or classifying of nodes, for example according to their location, from outer to inner, below the skin.

It is of especial advantage for the tree-type structure to be built-up according to the length of the lactiferous ducts. Similarly, the structure could be also configured or sorted according to the number of branches of the lactiferous ducts. Of particular advantage is a combination of these parameters.

With the method described herein, it is now possible to locate or localize unequivocally any objects in a breast, in particular a tumor, in a simple way and manner. The method is substantially stable and robust to a deformation of the breast and, therefore, can be performed substantially independently from an instrument. It also permits a comparison between and a fusion and superposition of different three-dimensional recordings. These three-dimensional recordings may be generated also by different modalities, such as computer tomography (CT), magnetic resonance tomography (MRT), positron emission tomography (PET), ultrasonography (US) and/or optical frequency comb technology (OFCT). Fusion is here understood to be a superposition of data of one and the same object of examination, with the data having been generated either at different points of time and/or by different instruments, and/or methods. A data fusion is usually performed in an image space, i.e. layer and/or volume data are oriented with respect to each other and scaled, so that coincidence with respect to locality is achieved. Depending upon the imaging modality, this kind of fusion may be inaccurate or even impossible if attended, for example, by too strong or too irregular a distortion and scaling. With the method described herein, however, a fusion of the data in the feature space is possible. Thereby, it is possible to obtain coincidence of the substantial extracted information. Furthermore, the extracted features such as, for example, the identified glandular bodies, or their centers of mass, can be used as reference points for a correction of distortion and adaptation of the image data of different modalities.

Using the uniform structure-description, it is possible to combine also further data such as, for example, sizes of glandular bodies and tumor adhesions, in addition to image data. The data obtained here may be used also for subsequent computer aided diagnosis (CAD), computer assisted surgery (CAS), and intervention planning (such as surgical intervention planning). It is also possible to monitor a development of diseases such as inflammations of individual ducts, abscesses, cysts, pseudo knots, fibroadenomas (tumors of connective tissue) over a long period.

In accordance with the method described herein, systems may be configured to perform the method. For example, an image-producing instrument for producing three-dimensional images, in particular an X-ray CT scanner, may be configured to perform the method described herein. In another example, an expert system for diagnosis may be configured to perform the method described herein. Other systems which may be similarly configured may include but are not limited to ultrasound scanners and nuclear spin tomographs. In any case, systems may include a storage medium having program instructions which are executable by a processor for performing the method described herein. In general, the term "storage medium", as used herein, may refer to any electronic medium configured to hold one or more set of program instructions, such as but not limited to a read-only memory, a random access memory, a magnetic or optical disk, or magnetic tape. The term "program instructions" may generally refer to commands within a program which are configured to perform a particular function.

It will be appreciated to those skilled in the art having the benefit of this disclosure that this invention is believed to provide a method and a system for determining a position of an object within a breast of a female patient. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. An X-ray machine having a non-transitory computer-readable medium encoded with program instructions which, when executed by a processor of the x-ray machine, comprises:
    producing a three-dimensional image of a breast;
    identifying lactiferous ducts and associated glandular bodies in the image;
    determining a position of an object relative to at least one of the lactiferous ducts and glandular bodies;
    recording the relative position in the computer-readable medium; and
    thereafter re-determining the position of the object from the previously recorded relative position even through orientation or configuration of the breast has changed.

2. The X-ray machine according to claim 1, wherein the three-dimensional image of the breast is produced with at least one of an X-ray computer tomography machine, an ultrasound scanner, and a nuclear spin tomograph.

3. The X-ray machine according to claim 1, further comprising identifying a nipple in the image prior to, subsequent, or during the step of identifying the lactiferous ducts and associated glandular bodies in the image.

4. The method X-ray machine according to claim 3, wherein identifying the nipple comprises contour segmentation of the breast and identification of the nipple on a basis of geometrical estimates.

5. The X-ray machine according to claim 1, wherein identifying lactiferous ducts and associated glandular bodies comprises threshold value segmentation of lactiferous ducts and geometrical segmentation of lactiferous ducts and glandular bodies.

6. The X-ray machine according to claim 1, wherein identifying lactiferous ducts and associated glandular bodies comprises utilizing a Snakes algorithm or another contour finding algorithm.

7. The X-ray machine according to claim 1, wherein determining a position of an object comprises establishing at least one feature of a spatial relationship between the object and at least one of the lactiferous ducts and glandular bodies.

8. The X-ray machine according to claim 7, wherein determining a position of an object comprises identifying at least one of the lactiferous ducts and glandular bodies with which the object has contact.

9. The X-ray machine according to claim 7, wherein determining a position of an object comprises determining a distance of the object from at least one of the lactiferous ducts and glandular bodies.

10. The X-ray machine according to claim 9, wherein the distance is established with respect to a center of mass of one of glandular bodies.

11. The X-ray machine according to claim 1, further comprising transposing the image to a simplified model subsequent to the step of identifying the lactiferous ducts and the associated glandular bodies.

12. The X-ray machine according to claim 11, wherein the simplified model is a tree-type data structure, with branches of the tree-type structure corresponding to lactiferous ducts, and leaves of the tree-type structure corresponding to glandular bodies.

13. The X-ray machine according to claim 1, further comprising:
producing a different three-dimensional image of the breast;
identifying lactiferous ducts and associated glandular bodies in the different image;
determining a position of the object within the different image relative to at least one of the lactiferous ducts and glandular bodies in the different image; and
fusing data of the three-dimensional images to coincide the determined positions of the object.

14. An X-ray machine comprising a non-transitory computer-readable medium encoded with program instructions which, when executed by a processor of the X-ray machine, comprises:
producing a three-dimensional image of a breast;
identifying lactiferous ducts and associated glandular bodies in the image;
determining a position of an object within the breast relative to at least one of the lactiferous ducts and glandular bodies; and
generating data of a model representing the identified lactiferous ducts and associated glandular bodies in the image and the determined position of the object related to at least one of the lactiferous ducts and glandular bodies.

15. The X-ray machine according to claim 14, wherein the program instructions are further executable by the processor for identifying a nipple in the image prior to, subsequent, or during the step of identifying the lactiferous ducts and associated glandular bodies in the image.

16. The X-ray machine according to claim 15, wherein the program instructions for identifying the nipple comprise program instructions for contour segmentation of the breast and identification of the nipple on a basis of geometrical estimates.

17. The X-ray machine according to claim 14, wherein the program instructions for identifying lactiferous ducts and associated glandular bodies comprise program instructions threshold value segmentation of lactiferous ducts and geometrical segmentation of lactiferous ducts and glandular bodies.

18. The X-ray machine according to claim 14, wherein the program instructions for identifying lactiferous ducts and associated glandular bodies comprise a Snake algorithm or another contour finding algorithm.

19. The X-ray machine according to claim 14, wherein the program instructions for determining the position of the object comprise program instructions for establishing at least one feature of a spatial relationship between the object and at least one of the lactiferous ducts and glandular bodies.

* * * * *

UNITED STATES PATENT AND TRADEMARK OFFICE
CERTIFICATE OF CORRECTION

PATENT NO. : 8,199,993 B2  Page 1 of 1
APPLICATION NO. : 12/401976
DATED : June 12, 2012
INVENTOR(S) : Kalender et al.

It is certified that error appears in the above-identified patent and that said Letters Patent is hereby corrected as shown below:

IN THE CLAIMS:

In col. 8, claim 14, line 13: please delete "related" and substitute --relative--.

Signed and Sealed this
Fourth Day of September, 2012

David J. Kappos
*Director of the United States Patent and Trademark Office*